United States Patent
Sharma et al.

(10) Patent No.: US 10,378,558 B2
(45) Date of Patent: Aug. 13, 2019

(54) AIR TREATMENT CHEMICAL DISPENSER HAVING ANGLED DISPERSION OF CHEMICALS

(71) Applicant: S.C. Johnson & Son, Inc., Racine, WI (US)

(72) Inventors: Nitin Sharma, Kenosha, WI (US); Deliang Shi, Kenosha, WI (US); Gerald W. Cummings, Pleasant Prairie, WI (US); Lina Long, Mount Prospect, IL (US); Paul E. Furner, Racine, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 313 days.

(21) Appl. No.: 14/025,913

(22) Filed: Sep. 13, 2013

(65) Prior Publication Data
US 2015/0078921 A1    Mar. 19, 2015

(51) Int. Cl.
*F04F 1/18* (2006.01)
*A01M 1/20* (2006.01)
(Continued)

(52) U.S. Cl.
CPC .............. *F04F 1/18* (2013.01); *A01M 1/2033* (2013.01); *A61L 9/122* (2013.01); *F04D 17/16* (2013.01);
(Continued)

(58) Field of Classification Search
CPC .............. A01M 1/2022; A01M 1/2027; A01M 1/2033; F04F 1/18; F04D 17/16
(Continued)

(56) References Cited

U.S. PATENT DOCUMENTS

| 2,585,339 A | 2/1952 | Miller |
| 2,614,820 A | 10/1952 | Boydjieff |
| (Continued) | | |

FOREIGN PATENT DOCUMENTS

| WO | 2005063013 A1 | 7/2005 |
| WO | 2009065629 A1 | 5/2009 |
| (Continued) | | |

OTHER PUBLICATIONS

PCT/US2014/055101 International Search Report and Written Opinion dated Jan. 9, 2015.
(Continued)

*Primary Examiner* — Dominick L Plakkoottam
*Assistant Examiner* — Connor J Tremarche
(74) *Attorney, Agent, or Firm* — Quarles & Brady LLP

(57) ABSTRACT

A device for dispensing an air treatment chemical includes a housing having an inlet for permitting air to enter into an interior space of the housing and an outlet for permitting air mixed with air treatment chemical to exit the interior space of the housing. A substrate positioned within the housing bears the air treatment chemical. A power supply mounted within the housing powers a motor mounted within the housing. The motor is connected to an impeller mounted within the housing. The impeller moves air from the inlet adjacent the substrate to mix the air treatment chemical into the moving air and deliver the mixture of air and air treatment chemical through the outlet to outside of the housing. The housing includes a transitional body defining a convergent-divergent channel for compressing the mixture at the converging section and expanding the mixture at the diverging section.

23 Claims, 12 Drawing Sheets

(51) Int. Cl.
*A61L 9/12* (2006.01)
*F04D 17/16* (2006.01)
(52) U.S. Cl.
CPC ......... *A61L 9/125* (2013.01); *A61L 2209/134* (2013.01)
(58) Field of Classification Search
USPC ........................................ 417/66; 261/30, 84
See application file for complete search history.

(56) References Cited

U.S. PATENT DOCUMENTS

| | | | |
|---|---|---|---|
| 2,764,789 A | 10/1956 | Zelenka | |
| 3,633,881 A | 1/1972 | Yurdin | |
| 3,941,283 A | 3/1976 | Siegfried | |
| 4,059,422 A | 11/1977 | Steiner | |
| 4,111,655 A | 9/1978 | Quincey | |
| 4,268,285 A | 5/1981 | Mason | |
| 4,294,778 A | 10/1981 | DeLuca | |
| 4,301,095 A | 11/1981 | Mettler et al. | |
| 4,377,399 A | 3/1983 | Bryson | |
| 4,396,557 A | 8/1983 | DeLuca | |
| 4,830,791 A | 5/1989 | Muderlak et al. | |
| 4,931,224 A | 6/1990 | Holzner, Sr. | |
| 5,126,078 A | 6/1992 | Steiner et al. | |
| 5,147,582 A | 9/1992 | Holzner, Sr. et al. | |
| 5,250,265 A | 10/1993 | Kiyoshi et al. | |
| 5,342,584 A | 8/1994 | Fritz et al. | |
| 5,358,443 A | 10/1994 | Mitchell et al. | |
| 5,370,829 A | 12/1994 | Kunze | |
| 5,435,817 A | 7/1995 | Davis et al. | |
| 5,498,397 A * | 3/1996 | Horng ................ | A61L 9/122 261/DIG. 88 |
| 5,547,616 A | 8/1996 | Dancs et al. | |
| 5,616,172 A | 4/1997 | Tuckerman et al. | |
| 5,620,306 A | 4/1997 | Day | |
| 5,641,343 A | 6/1997 | Frey | |
| 5,695,692 A | 12/1997 | Kennedy | |
| 5,711,033 A * | 1/1998 | Green ................ | A42B 3/286 2/171.3 |
| 5,753,000 A | 5/1998 | Chiu et al. | |
| 5,829,188 A | 11/1998 | Tanitomi | |
| 5,837,020 A | 11/1998 | Cartellone | |
| 5,840,092 A | 11/1998 | Rick et al. | |
| 5,925,172 A | 7/1999 | Rick et al. | |
| 5,932,147 A | 8/1999 | Chen | |
| 5,997,619 A * | 12/1999 | Knuth ................ | A61L 9/20 55/356 |
| 6,042,333 A | 3/2000 | Day | |
| 6,050,551 A | 4/2000 | Anderson | |
| 6,053,968 A * | 4/2000 | Miller ................ | A61L 9/20 96/16 |
| 6,061,950 A | 5/2000 | Carey et al. | |
| 6,102,660 A | 8/2000 | Lee | |
| 6,103,201 A | 8/2000 | Green | |
| 6,156,085 A | 12/2000 | Chiu et al. | |
| 6,241,218 B1 | 6/2001 | Tanitomi | |
| 6,254,065 B1 | 7/2001 | Ehrensperger et al. | |
| 6,293,044 B1 | 9/2001 | Feng | |
| 6,315,821 B1 | 11/2001 | Pillion et al. | |
| 6,328,791 B1 | 12/2001 | Pillion et al. | |
| 6,371,450 B1 | 4/2002 | Davis et al. | |
| 6,392,549 B1 | 5/2002 | Wu | |
| 6,435,828 B1 | 8/2002 | Bostwick | |
| 6,447,587 B1 | 9/2002 | Pillion et al. | |
| 6,482,365 B1 | 11/2002 | Soller | |
| 6,497,753 B1 | 12/2002 | Gutmann | |
| 6,508,868 B2 | 1/2003 | Pillion et al. | |
| 6,511,531 B1 * | 1/2003 | Cartellone ................ | A61L 9/03 261/142 |
| 6,514,052 B2 | 2/2003 | Bostwick | |
| 6,553,711 B1 | 4/2003 | Feng | |
| 6,569,387 B1 | 5/2003 | Furner et al. | |
| 6,623,265 B1 | 9/2003 | Day | |
| 6,631,888 B1 | 10/2003 | Prueter | |
| 6,666,660 B2 * | 12/2003 | Kegg ................ | F04D 29/663 15/326 |
| 6,719,217 B1 | 4/2004 | Tawara et al. | |
| 6,769,631 B2 | 8/2004 | Brown | |
| 6,854,208 B1 * | 2/2005 | Chuang ................ | A01M 1/2027 261/84 |
| 6,913,733 B2 * | 7/2005 | Hardy ................ | A61L 9/014 422/124 |
| 6,926,902 B2 | 8/2005 | Inoue et al. | |
| 7,008,180 B2 | 3/2006 | Fujimori et al. | |
| 7,040,548 B2 | 5/2006 | Rodgers | |
| 7,112,232 B2 | 9/2006 | Chang et al. | |
| 7,138,130 B2 | 11/2006 | Davis et al. | |
| 7,168,630 B1 | 1/2007 | Ketcha et al. | |
| 7,175,815 B2 | 2/2007 | Yamasaki et al. | |
| 7,285,248 B2 | 10/2007 | Yamamoto et al. | |
| 7,316,729 B2 | 1/2008 | Paterson et al. | |
| 7,431,901 B2 | 10/2008 | Stiros et al. | |
| 7,459,168 B2 | 12/2008 | Inoue et al. | |
| 7,537,647 B2 * | 5/2009 | Adair ................ | B01D 45/06 261/DIG. 88 |
| 7,585,344 B2 | 9/2009 | Paterson et al. | |
| 7,597,857 B2 | 10/2009 | Reece | |
| 7,748,687 B2 | 7/2010 | Pankhurst et al. | |
| 7,789,921 B2 * | 9/2010 | Thurin ................ | B01D 46/0028 55/282 |
| 7,811,348 B2 | 10/2010 | Paterson et al. | |
| 7,833,492 B2 | 11/2010 | Schumacher et al. | |
| 7,887,759 B2 | 2/2011 | Triplett | |
| 7,887,760 B2 * | 2/2011 | Yamamoto .......... | A01M 1/2033 422/124 |
| 7,892,487 B2 | 2/2011 | Adair et al. | |
| 7,917,018 B2 | 3/2011 | Schumacher et al. | |
| 7,922,589 B2 | 4/2011 | Kuhn et al. | |
| 8,025,845 B2 | 9/2011 | Yamasaki et al. | |
| 8,048,379 B2 | 11/2011 | Sassoon | |
| 8,137,629 B2 | 3/2012 | Faber et al. | |
| 8,197,761 B1 | 6/2012 | Miller-Larry | |
| 8,282,883 B2 | 10/2012 | Yamasaki et al. | |
| 8,303,385 B2 | 11/2012 | Park | |
| 8,367,011 B2 | 2/2013 | Yamamoto | |
| 8,385,730 B2 | 2/2013 | Bushman et al. | |
| 8,435,450 B2 | 5/2013 | Kawamura et al. | |
| 8,449,828 B2 | 5/2013 | Yamamoto et al. | |
| 8,469,293 B2 | 6/2013 | Doty et al. | |
| 2003/0012680 A1 | 1/2003 | Balsys | |
| 2003/0175171 A1 * | 9/2003 | Yamamoto .......... | A01M 1/2033 422/124 |
| 2005/0019165 A1 | 1/2005 | Fujimori et al. | |
| 2005/0123423 A1 * | 6/2005 | Weisser ................ | F04D 29/083 417/423.7 |
| 2005/0191217 A1 | 9/2005 | Selander | |
| 2006/0039835 A1 | 2/2006 | Nottingham et al. | |
| 2006/0043619 A1 | 3/2006 | Brown et al. | |
| 2006/0137241 A1 | 6/2006 | Yamasaki et al. | |
| 2007/0036673 A1 | 2/2007 | Selander | |
| 2007/0180801 A1 | 8/2007 | Paterson et al. | |
| 2007/0180996 A1 * | 8/2007 | Paterson ................ | B03C 3/32 96/60 |
| 2007/0277487 A1 * | 12/2007 | Thurin ................ | B01D 46/0028 55/471 |
| 2009/0008411 A1 | 1/2009 | Schumacher et al. | |
| 2009/0060799 A1 | 3/2009 | Torres | |
| 2009/0183636 A1 | 7/2009 | Levine et al. | |
| 2010/0025490 A1 | 2/2010 | Bushman et al. | |
| 2010/0064895 A1 | 3/2010 | Thurin et al. | |
| 2010/0090022 A1 | 4/2010 | Hayashida | |
| 2010/0132246 A1 * | 6/2010 | Ohtsuka ................ | A01M 1/2033 43/133 |
| 2010/0269826 A1 | 10/2010 | Colombo et al. | |
| 2011/0027124 A1 * | 2/2011 | Albee ................ | A61L 9/122 422/5 |
| 2011/0038761 A1 | 2/2011 | Saleh et al. | |
| 2011/0108633 A1 | 5/2011 | Yamamoto et al. | |
| 2011/0108634 A1 | 5/2011 | Yamamoto et al. | |
| 2011/0110827 A1 | 5/2011 | Yamamoto et al. | |
| 2011/0116977 A1 | 5/2011 | Yamamoto et al. | |
| 2011/0139889 A1 | 6/2011 | Ohtsuka et al. | |

(56) References Cited

U.S. PATENT DOCUMENTS

| | | |
|---|---|---|
| 2011/0221079 A1 | 9/2011 | Yamasaki et al. |
| 2012/0180666 A1 | 7/2012 | Lim et al. |
| 2012/0181350 A1 | 7/2012 | Snider |
| 2012/0183280 A1 | 7/2012 | Kowalec et al. |
| 2012/0205462 A1 | 8/2012 | Burke et al. |
| 2012/0261484 A2 | 10/2012 | Blaylock et al. |
| 2012/0273978 A1 | 11/2012 | Sharma |
| 2012/0275932 A1 | 11/2012 | Sharma |
| 2013/0032641 A1 | 2/2013 | Muderlak et al. |
| 2013/0049236 A1 | 2/2013 | Garon et al. |
| 2013/0093108 A1 | 4/2013 | Scolari |
| 2013/0328223 A1 | 12/2013 | Sharma et al. |

FOREIGN PATENT DOCUMENTS

| | | |
|---|---|---|
| WO | 2011019404 A2 | 2/2011 |
| WO | 2011106889 A1 | 9/2011 |
| WO | 2011126208 A2 | 10/2011 |
| WO | WO 2013/188493 A1 | 12/2013 |

OTHER PUBLICATIONS

International Preliminary Report on Patentability dated Mar. 24, 2016, International App. No. PCT/US2014/055101, 9 pages.

\* cited by examiner

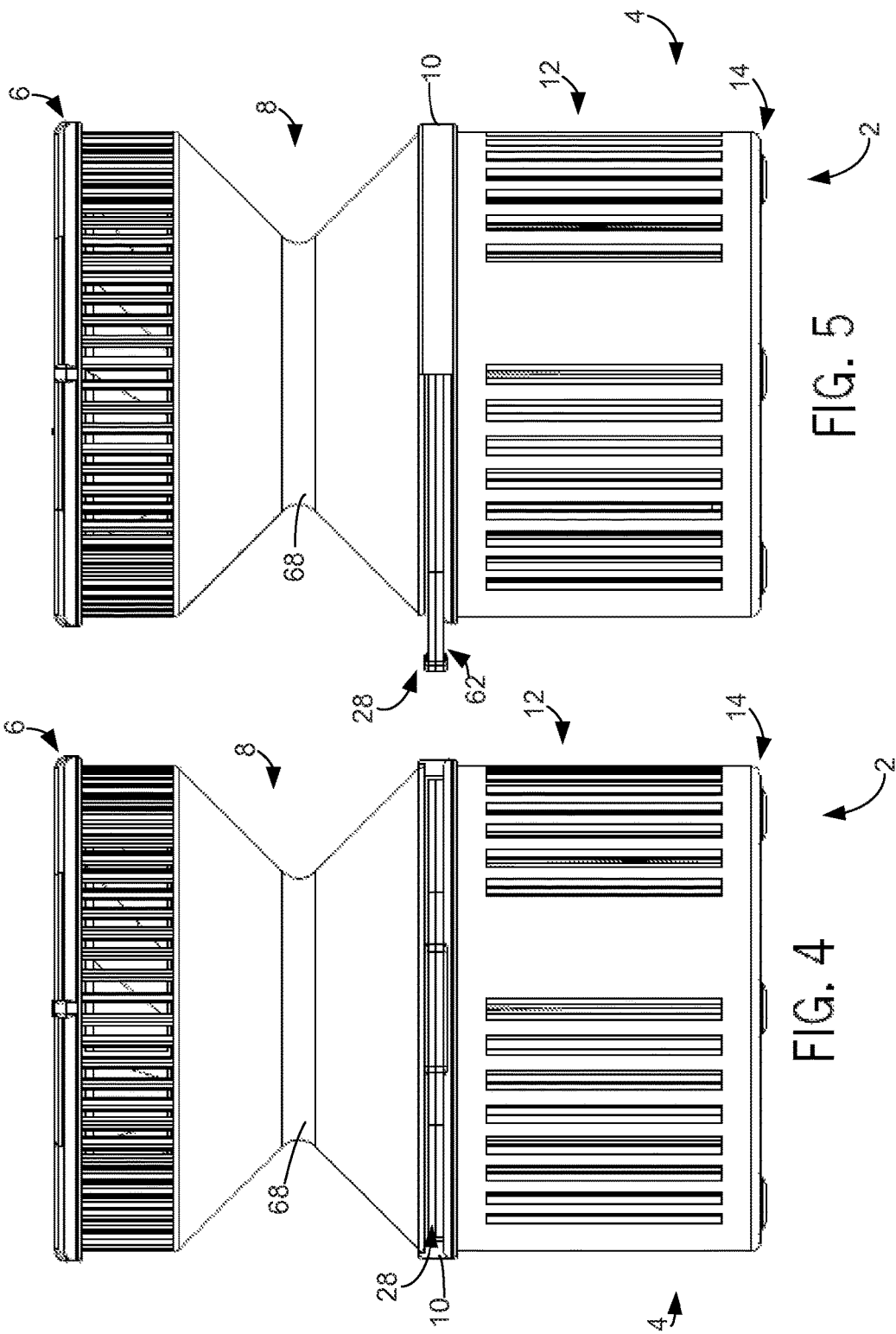

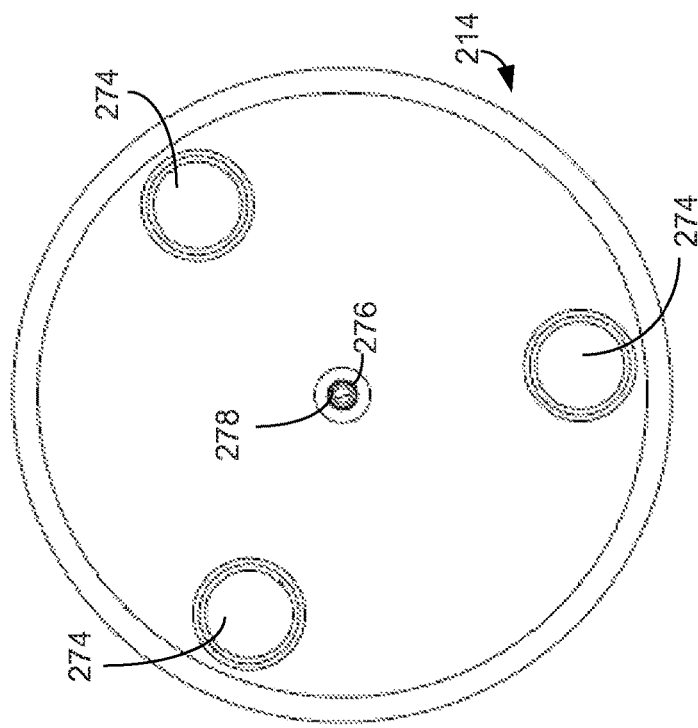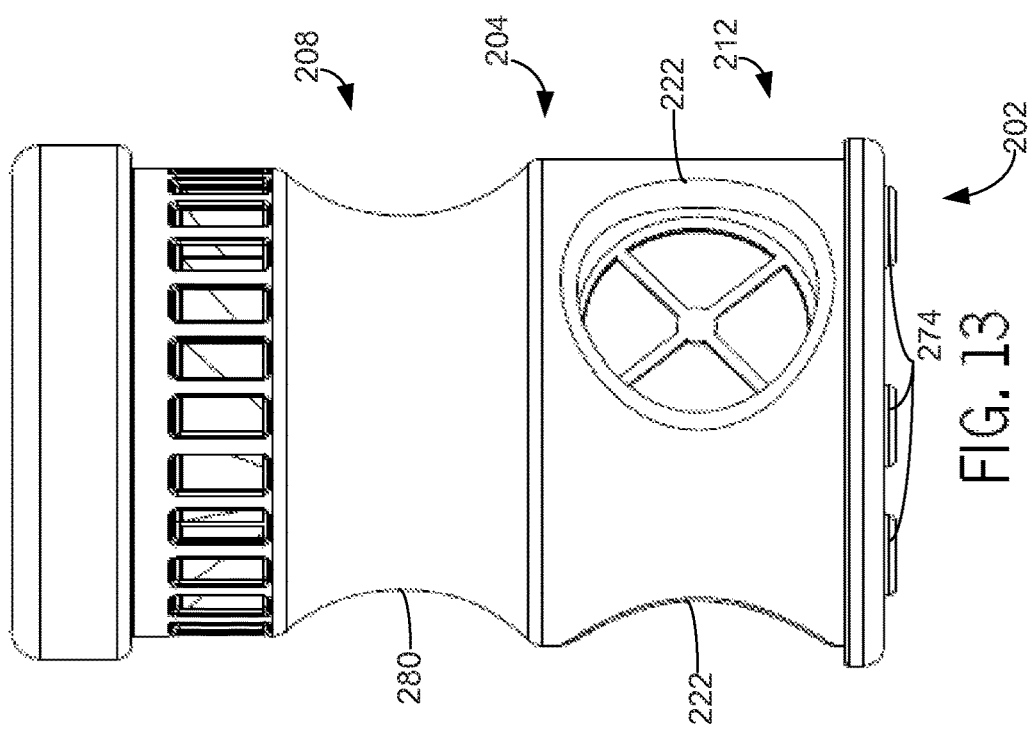

AIR TREATMENT CHEMICAL DISPENSER HAVING ANGLED DISPERSION OF CHEMICALS

CROSS REFERENCE TO RELATED APPLICATIONS

Not applicable

REFERENCE REGARDING FEDERALLY SPONSORED RESEARCH OR DEVELOPMENT

Not applicable

BACKGROUND OF THE INVENTION

1. Field of the Invention

The present invention relates to portable devices that dispense chemicals such as insect repellents and/or fragrances.

2. Description of the Background

Various techniques have been developed to provide humans with protection from insect bites. For insect control inside buildings a primary emphasis is placed on trying to keep insects from entering the building at all (e.g. placing screens over windows). This sometimes is supplemented with chemical treatment of room air and/or the use of traps. See e.g. U.S. Pat. Nos. 6,582,714 and 7,175,815, and also U.S. patent application publications 2005/0079113, 2006/0039835, 2006/0137241 and 2007/0036688.

When an individual is outdoors where the area cannot be effectively screened, and the individual is mostly staying in a particular area (e.g. at a picnic, or on a patio near a building), traps and repellents are the primary focus. For instance, the individual can apply an insect repellent to clothing or directly to their skin. However, some individuals may be averse to applying chemicals onto delicate clothing or directly onto the skin. Such individuals may avoid products which direct that type of application. Further, if an individual removes an outer layer of clothing sprayed with the insect repellent, that individual must reapply or else have a higher risk of insect bites.

Another means for providing protection to humans from insect bites is to infuse a general area with insect repellant by use of candles (e.g. citronella candles) or other dispensing devices which disperse repellents into the air. These dispensing devices may be electrical devices that actively distribute the repellent by use of fans for evaporating an insecticide source, automatic sprays of liquid repellent, heating elements with wicks, and the like. The devices may be mounted to a surface, such as a wall or a table top, or rested thereon. A common electrical dispenser for distributing insect repellent includes an insecticide source housed within the dispenser that further provides a fan to blow air past the insecticide source and dispense the material into the air. The insecticide source is often a substrate impregnated with insect repellent or other air treatment chemicals and can accommodate a flow of air through the substrate when used in conjunction with a fan.

However, present electrical devices have drawbacks of limited coverage area. For instance, devices that cannot distribute the active far enough have dramatically reduced protective capabilities to individuals located outside the periphery of the coverage area. In some cases, coverage area is limited due to constraints on electrical power availability, fan size, and motor power requirements that are necessarily in place for meeting certain design factors, such as those required for achieving lightweight, portable dispensers. Attempts to increase the repellent coverage area include increasing the fan speed and/or providing more power to the motor. However, such modifications often lead to increased fan noise that may be a nuisance in the environment and higher power consumption which may be costly and demand more frequent battery replacements. Other attempts include increasing the size of the electrical dispensers and/or utilizing multiple dispensers. However, such solutions may result in bulky and burdensome devices that are not easily portable.

Hence, a need exists for improved devices for dispensing insect control actives and other air treatment chemicals, particularly those that can provide an increased coverage area while maintaining portability and ease of use.

SUMMARY OF THE INVENTION

In one embodiment the invention provides a device for dispensing an air treatment chemical, where the device has: (a) a housing including an inlet for permitting air to enter into an interior space of the housing and including an outlet for permitting air mixed with air treatment chemical to exit the interior space; (b) a substrate positioned within the housing and bearing the air treatment chemical; (c) a power supply mounted within the housing; (d) a motor mounted within the housing and being powered by the power supply; and (e) an impeller mounted within the housing and connected to the motor, the impeller being capable of moving air from the inlet adjacent the substrate so as to mix the air treatment chemical into the moving air, and then deliver a mixture of air and air treatment chemical through the outlet to outside of the housing. The housing includes a transitional body that defines a convergent-divergent channel in which the mixture compresses, at a converging section, toward a throat of the convergent-divergent channel and expands, at a diverging section, away from the throat and through the outlet of the housing.

In one aspect, the converging section is positioned below the diverging section of the convergent-divergent channel. A lower end of the converging section is proximate to the substrate positioned within the housing. In another aspect, a plurality of substrates are stacked proximate to the lower end of the converging section. In further aspects, an upper end of the diverging section is configured to receive a top cover and provide a plurality of outlet slots for the outlet. In yet another aspect, the impeller extends through at least a portion of the diverging section of the convergent-divergent channel. The housing further comprises a refill retainer that is in operative connection with the converging section and a battery module, such that the refill ring is configured to receive the at least one substrate or the plurality of substrates in a stacked position. The battery module includes a cylindrical wall extending from a base and having a plurality of inlet slots.

In another embodiment the invention provides a device for dispensing an air treatment chemical, where the device has: (a) a housing including an inlet for permitting air to enter into an interior space of the housing and including an outlet for permitting air mixed with air treatment chemical to exit the interior space, whereby the inlet is provided below the outlet on the housing; (b) a substrate positioned within the housing, the substrate bearing the air treatment chemical; (c) a power supply mounted within the housing; (d) a motor mounted within the housing and being powered by the power supply; and (e) an impeller mounted within the housing and connected to the motor, the impeller comprising an enclosed impeller having multiple channels. The housing provides a convergent-divergent channel in which the mixture compresses, at a converging section, toward a throat of the convergent-divergent channel and expands, at a diverging section, away from the throat and through the outlet of the housing.

In one aspect, the impeller is mounted in operative connection to a top cover of the housing, whereby the top cover of the housing is configured to be received on an upper end of the diverging section of the convergent-divergent channel. The multiple channels of the impeller extend through at least a portion of the diverging section of the convergent-divergent channel. In another aspect, the multiple channels are sloped parallel to the diverging section of the convergent-divergent channel. In further aspects, the multiple channels are angled opposite to the direction of rotation of the impeller. It is contemplated that the multiple channels of the fan include about 10 channels to about 20 channels.

In other aspects, the convergent-divergent channel defines about a 75 degree to about a 105 degree angle that has a vertex at the throat of the channel. The power supply is mounted to a top cover of the housing. In some embodiments, the power supply is mounted below the substrate positioned within the housing. A base portion of the housing includes a plurality of outlet slots and receives a plurality of substrates configured to be aligned with the plurality of outlet slots. It is contemplated that the plurality of substrates comprises two or three substrates.

In yet another embodiment the invention provides a device for dispensing an air treatment chemical, where the device has: (a) a housing including an inlet for permitting air to enter into an interior space of the housing and including an outlet for permitting air mixed with air treatment chemical to exit the interior space; (b) a plurality of substrates mounted within the housing, each of the plurality of substrates bearing the air treatment chemical; (c) a power supply mounted within the housing; (d) a motor mounted within the housing and being powered by the power supply; and (e) an impeller mounted within the housing and connected to the motor, the impeller being capable of moving air from the inlet adjacent the plurality of substrates so as to mix the air treatment chemical into the moving air, and then deliver a mixture of air and air treatment chemical through the outlet to outside of the housing. The housing provides a convergent-divergent channel that defines a flow pathway for the mixture, whereby the mixture compresses at a converging section toward a throat of the convergent-divergent channel and expands at a diverging section away from the throat and through the outlet of the housing. The impeller delivers the mixture at an inclined emission angle with respect to a plane defined by a top covering of the housing.

In one aspect, the inclined emission angle is about 20 degrees to about 70 degrees. The impeller comprises an enclosed impeller that has multiple channels. The multiple channels are sloped parallel to the diverging section of the convergent-divergent channel and angled opposite to the direction of rotation of the impeller.

These and other advantages of the present invention will become better understood upon consideration of the following detailed description and drawings and claims.

BRIEF DESCRIPTION OF THE DRAWINGS

FIG. 4 is a front view of the dispensing device of FIG. 1;

FIG. 5 is a side view of the dispensing device of FIG. 1;

FIG. 13 is a rear side view of the dispensing device of FIG. 9;

FIG. 14 is a bottom view of the dispensing device of FIG. 9;

Like reference numerals will be used to refer to like parts from Figure to Figure in the following description of the drawings.

DETAILED DESCRIPTION OF THE DRAWINGS

Figure 1:
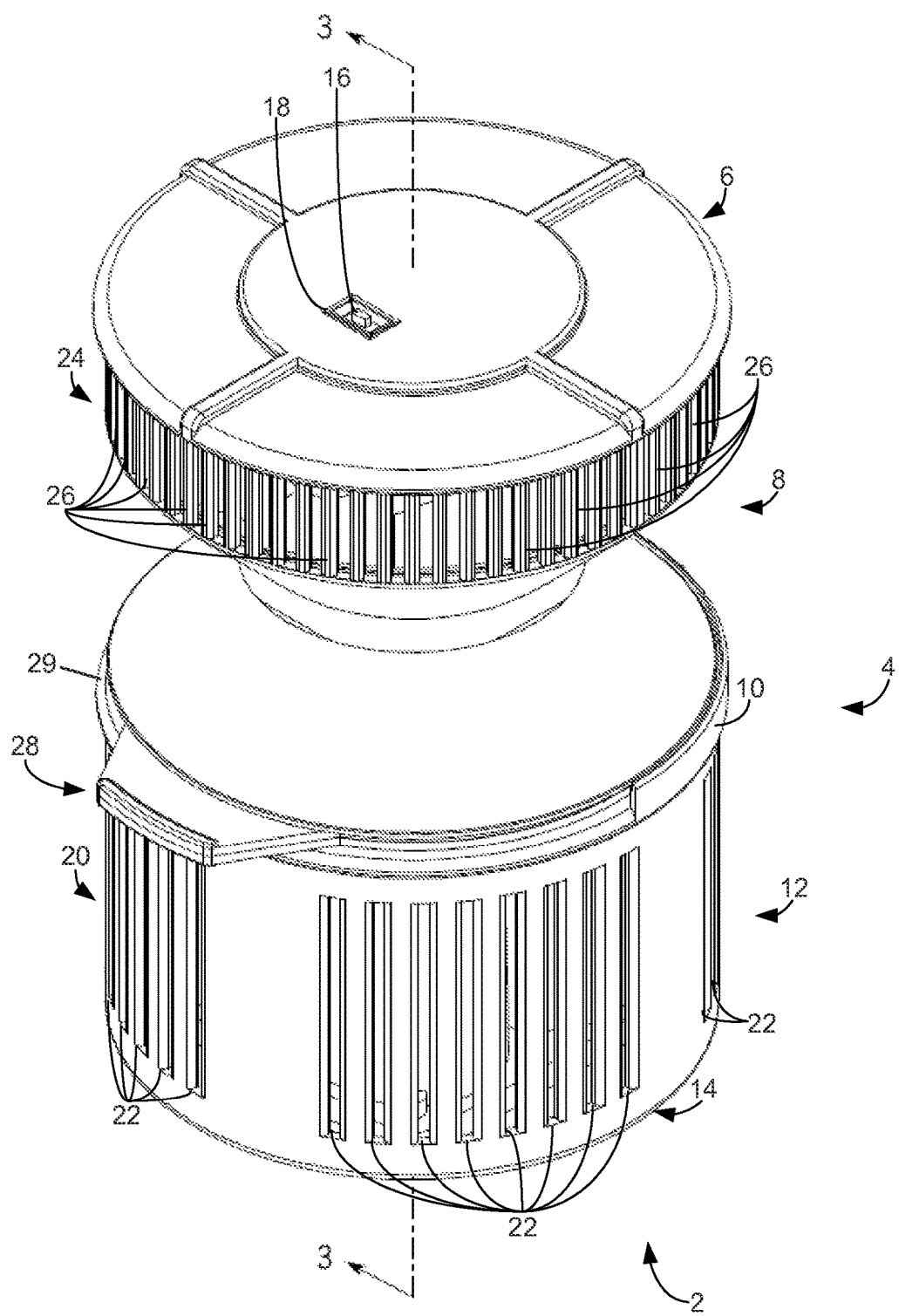
FIG. 1 is a top and side perspective view of a device for dispensing an air treatment chemical according to the invention.

FIGS. 1-8 illustrate one embodiment of a device 2 for dispensing an air treatment chemical. As shown in FIG. 1, the device 2 includes a housing 4 that comprises a top covering 6 disposed on a transitional body 8. The transitional body 8 is further disposed on a circular refill retainer 10 that rests on top of a base section 12. The base section 12 is a cylindrical-shaped structure that extends downward to a bottom support 14. The bottom support 14 is generally a circular-shaped surface transverse to the cylindrical structure and configured to engage a resting surface for setting the device 2, such as a table-top. It is contemplated that the device 2 is easily portable and lightweight. Further, the device 2 can be operated by an on/off switch 16 provided through a switch opening 18 disposed on the top covering 6. The configuration of the device 2 in FIG. 1 is illustrative of an exemplary configuration and is not intended to limit the present invention.

Further shown in FIG. 1, an air inlet grill 20 is provided on the cylindrical structure of the base section 12. The inlet grill 20 is characterized by a plurality of spaced-apart longitudinal inlet slots 22 disposed 360 degrees circumferentially around the base section 12. The inlet slots 22 permit outside air to enter the housing 4 and travel upward through the housing 4 to an outlet grill 24 provided on an upper end of the transitional body 8. The outlet grill 24 is generally a cylindrical ring that comprises a plurality of spaced-apart longitudinal outlet slots 26 or ribs disposed 360 degrees circumferentially about the upper end of the transitional body 8. Air flowing within the housing 4 exits the housing 4 through the outlet slots 26. It is contemplated that both the inlet slots 22 and the outlet slots 26 are long, narrow openings, and that the outlet slots 26 may be shorter, but more numerous and compacted than the inlet slots 22. The present invention, however, is not limited to any particular shapes, sizes, numbers or patterns of openings. For instance, the inlet slots 22 and the outlet slots 26 may extend about any partial or whole portion of the circumference of the housing 4.

Still referring to FIG. 1, the refill retainer 10 provides operative engagements for a lower end of the transitional body 8 and an upper end of the base section 12 above the inlet grill 20. The refill retainer 10 provides a slot 29 in the housing 4 for easy removal and insertion of a chemical substrate 28. In some embodiments, the refill retainer 10 provides attachment means, such as locking mechanisms, snaps, hinges, and the like, for securing to at least one of the transitional body 8 and the base section 12. In another aspect, the refill retainer 10 is manufactured integrally with one or both of the transitional body 8 and the base section 12.

Still in reference to FIG. 1, the chemical substrate 28 inserted at the refill retainer 10 extends about midsection of the housing 4. Specifically the chemical substrate 28 is positioned just above the inlet grill 20 on the base section 10 and extends into the path of the air moving between the inlet grill 20 and the outlet grill 24. The chemical substrate 28 bears at least one air treatment chemical that mixes into the moving air to be carried and released outside of the housing 4 when the device 2 is turned on. As such, the chemical substrate 28 is replaceable upon use-up of the air treatment chemical impregnated therein.

In particular, the chemical substrate 28 shown in FIG. 1 is formed from a substance that permits the moving air drawn through the inlet grill 20 to pass through it. The chemical substrate 28 may comprise a fabric, paper, or other fibrous material that is infused with the air treatment chemical, which may include an insecticide, fragrances, solvents, deodorizers and/or a mix thereof. The choice of the fabric material, its porosity, the speed of the moving air flow, and the vapor pressure of the air treatment chemical are some factors that are coordinated in achieving a particular use-up speed of the replaceable chemical substrate 28. An example refill unit has a twelve hour life until its infused air treatment chemical is completely diffused.

The chemical substrate 28 shown in FIG. 1 may comprise one of the fabric substrates described in U.S. Patent Application Publication No. 2011/0038761. For instance, by impregnating the fabric substrate with an appropriate air treatment chemical, air entering the device 2 will pick up some of the volatile air treatment chemical and dispense it out of the device 2. Active release rates of 0.2 milligrams per hour (mg./hr.) or higher are preferred. For use in controlling mosquitoes, preferred actives are transfluthrin, metofluthrin, prallethrin, vaporthrin, tefluthrin, and esbiothrin or other synthetic pyrethroids. Metofluthrin from the Sumitomo Chemical Company (trade name SumiOne) is particularly preferred. The impregnation material can be pure active, or for ease of handling the material can be dissolved in a hydrocarbon or other solvent. Alternatively, or in addition, the fabric bears a fragrance, a deodorizer, or other air treatment chemical. It is preferred to have the chemical substrate 28 configured so that the pressure drop across the substrate is no more than 40 Pascals (Pa). Suitable fabrics can be made of woven or non-woven materials providing only minimal resistance to the airflow.

The chemical substrate 28 should also be capable of holding active ingredient dosed onto the material and also allow ready migration of the active to the surface so as to allow its evaporation in response to the airflow. For an active ingredient that is hydrophobic and migrateable at common environmental temperatures between about 10° C. and 40° C. (e.g., metofluthrin), suitable materials include, only by way of example, polyester, polypropylene, cotton, cellulose, polyrayon, and other similar fabrics. These can be non-wovens with basis weights ranging from 10 grams per square meter (gsm) to 40 grams per square meter (gsm), fabricated from synthetic, natural, or combined synthetic and natural polymeric materials.

The ideal fabric substrate that forms the chemical substrate 28 should also allow for wicking of the active ingredient following dosing so as to ensure efficient distribution throughout the substrate, and thereafter allow migration of active ingredient to the substrate surface to replenish the active ingredient that is being evaporated by the passing airflow. Dosing may be by dropping, spraying, printing, or other conventional delivery of a liquid active ingredient to the substrate 28. A particularly desirable fabric is a non-woven felted material with a basis weight of 20-30 gsm fabricated from polyethylene terephthalate.

Figure 2:
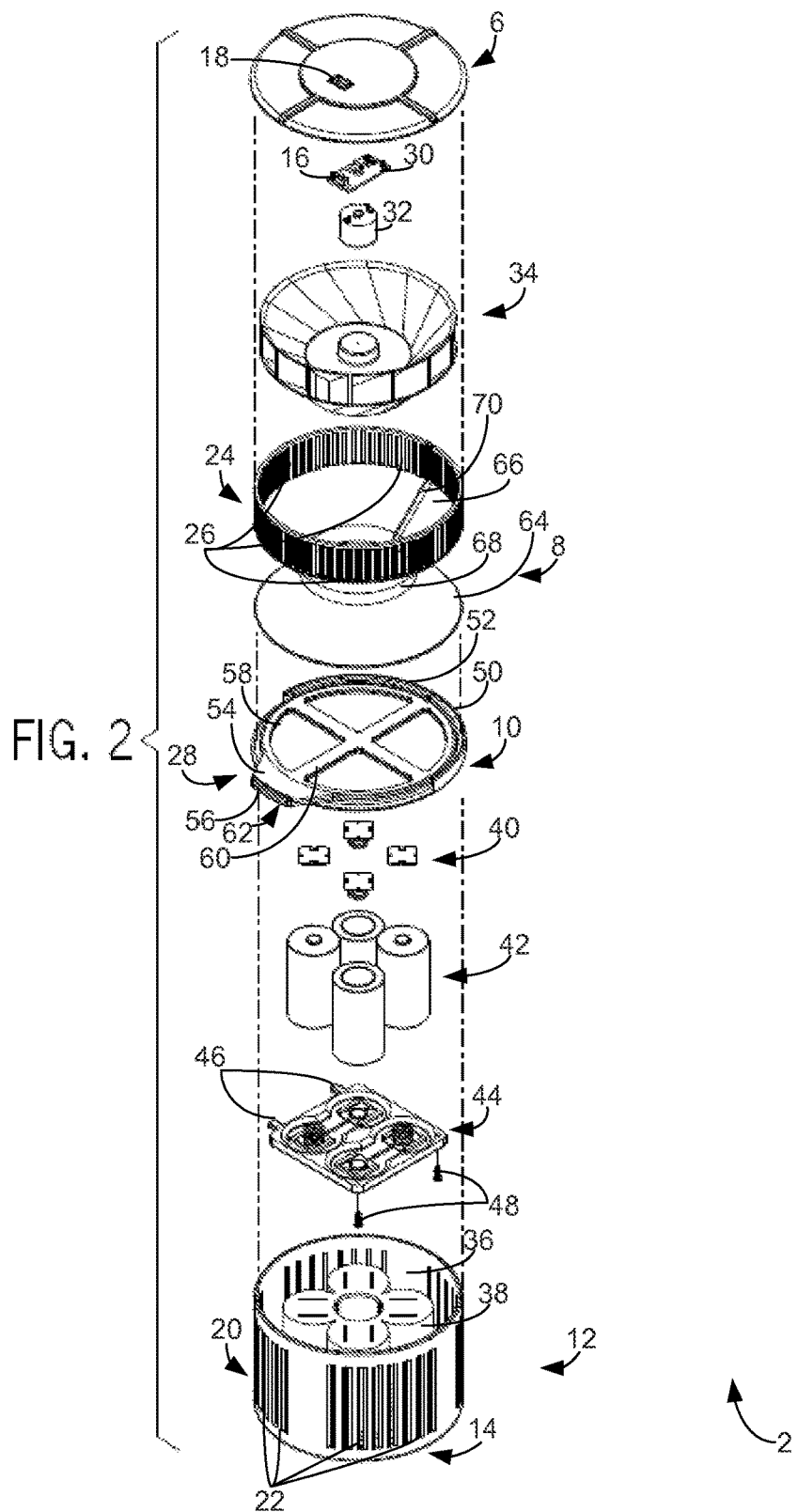
FIG. 2 is an exploded perspective view of the dispensing device of FIG. 1.

Turning now to FIG. 2, an exploded view of the device 2 shown in FIG. 1 is depicted. The top covering 6 is received on an upper portion of the transitional body 8 proximate the outlet grill 24 defined by the plurality of outlet slots 26. The top covering 6 acts as a lid for enclosing a switch board 30 having the on/off switch 16 provided thereon and aligned with the switch opening 18, a motor 32, and an impeller 34 mounted therein. The transitional body 8 joins an upper side of the refill retainer 10 that holds the chemical substrate 28, while the lower side of the refill retainer 10 joins the base section 12. The base section 12 provides the inlet grill 20 defined by the plurality of inlet slots 22 and further extends downward to the bottom support 14 disposed generally transverse thereof. When joined, the chemical substrate 28 and the base section 12 define an internal cavity 36 that receives incoming air around a centrally disposed battery module 38. The battery module 38 houses a set of battery leads 40 that are placed in operative contact with a set of batteries 42 inserted therein. A module door 44 attaches to the bottom support 14 and provides access to the battery module 38 for replacing batteries. As shown in FIG. 2, the module door 44 secures to the bottom support 14 by a pair of tabs 46 and a pair of set screws 48, although other securing means can be contemplated. It is noted that although batteries are provided for the present invention, other power supply means can be incorporated, such as solar power.

The chemical substrate 28 in FIG. 2 is received on the refill retainer 10 against an upstanding semicircular wall 50 provided about a periphery of the retainer 10. The semicircular wall 50 provides means for receiving and securing the lower portion of the transitional body 8, such as an indented ledge 52 for placement of a lower edge of the transitional body 8. The chemical substrate 28 disposed therein comprises a top frame 54, a bottom frame 56, and a fabric substrate 58 sandwiched between the frames 54, 56. At least one of the top frame 54 and the bottom frame 56 has a spoke support 60 spanning across the circular frame for supporting the fabric substrate 58 in the stream of moving air. The moving air passes through the portions of the fabric substrate 58 exposed between the spokes and evaporates the volatile chemical thereon. Further, the chemical substrate 28 provides a tab 62 on at least one of the top frame 54 and the bottom frame 56 for insertion and removal of the chemical substrate 28 in the refill retainer 10. It is contemplated that the chemical substrate 28 is slidingly inserted into and removed from the refill retainer 10. Further, it is contemplated that the refill retainer 10 is configured to receive a plurality of chemical substrates 28 disposed therein, such as two or three substrates 28 in a stacked configuration.

Still referring to FIG. 2, the transitional body 8 includes the lower circular edge that engages the refill retainer 10 and an upper circular edge having about the same diameter that engages the top covering 6. Between the edges of the transitional body 8 is a converging cone 64 fluidly connected to a diverging cone 66 at a throat 68 where the narrowed ends of the cones 64, 66 share a common diameter. As such, the transitional body 8 defines an interior space that provides a convergent-divergent channel for a flow of air, whereby the lower end of the converging cone 64 engages the refill retainer 10 and the upper end of the diverging cone 66 provides the plurality of outlet slots 26 and receives the top covering 6. In operation, the lower end of the converging cone 64 proximate the at least one chemical substrate 28 receives the air mixed with the chemical treatment into the transitional body 8. The mixture compresses as it flows through the converging cone 64 and upward toward the throat 68, and expands at the diverging cone 66 away from the throat 68 toward the outlet grill 24. It is contemplated that the convergent-divergent channel defines about a 75 degree to about a 105 degree angle A (see FIG. 3) having a vertex at the throat 68 of the channel, and more preferably the angle A is approximately 90 degrees.

Still in reference to FIG. 2, the diverging cone 66 of the transitional body 8 contains the impeller 34, which is operatively connected to the motor 32 engaging a central portion of the impeller 34. The motor 32 is further connected to the switch board 30 that provides the on/off switch 16 for controlling the motor 32. In the on position, the motor 32 provides power from the set of batteries 42 to propel the impeller 34. The impeller 34 operates to pull air through the inlet grill 20 into the internal cavity 36 of the base section 12, and vacuums the air through the chemical substrate 28 upward into the converging-diverging internal space of the transitional body 8. A wire channel 70 may be provided as a grooved channel on the inner surface of the transitional body 8 for guiding a wire (not shown) that feeds power from the power supply in the base section 12 to the motor 32. The wire channel 70 may continue along the inner face of the top covering 6. In practice, the top covering 6 need not be removed. As such, it is contemplated that the top covering 6 is designed to be securely fastened to the transitional body 8 by screws, glue, or other means, however, more removable connections can be contemplated, such as twist-lock interactions, hinges and the like.

Figure 3:
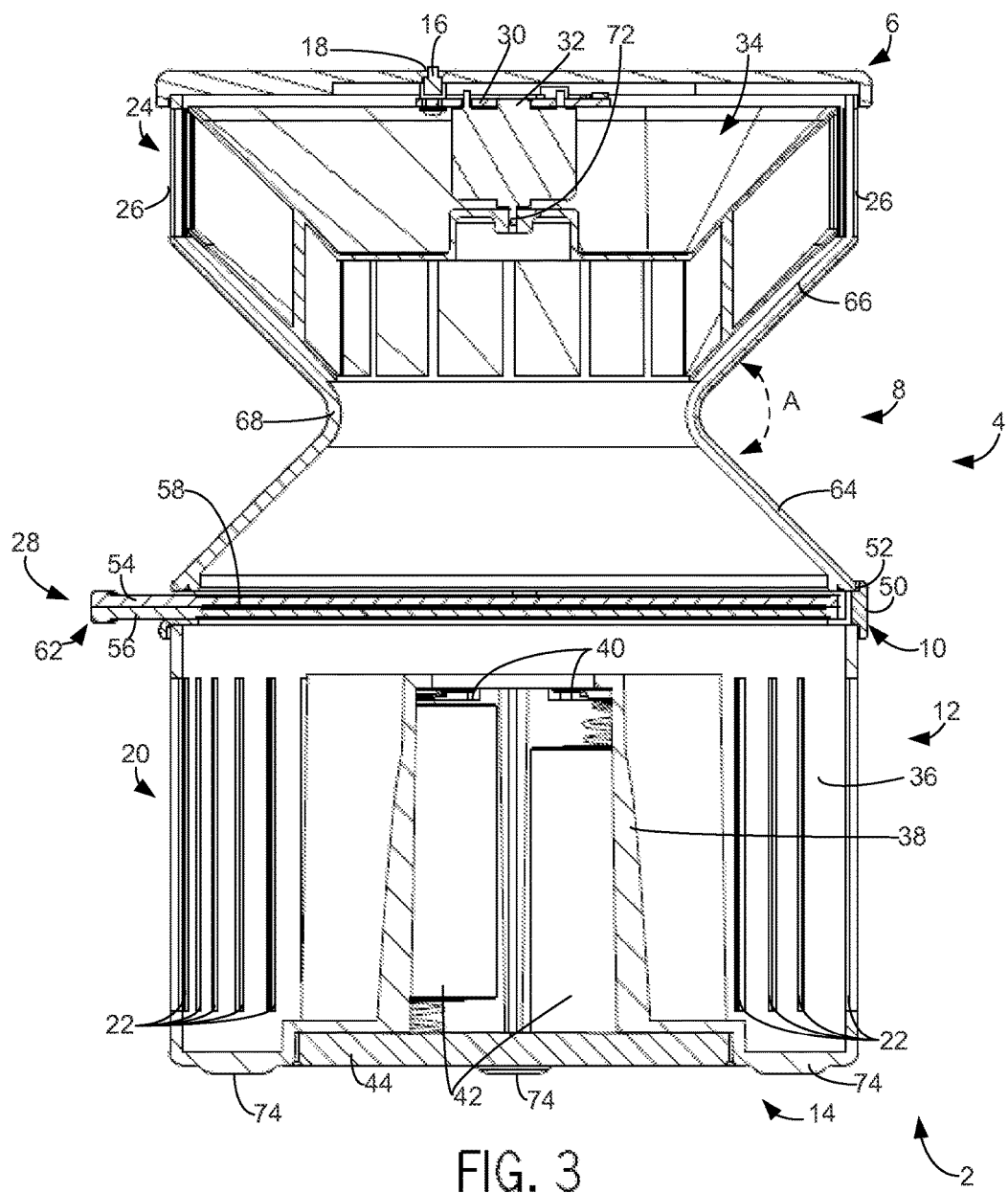
FIG. 3 is a cross-sectional view taken along line 3-3 of FIG. 1.

Moving now to FIG. 3, a cross-section taken along line 3-3 of FIG. 1 shows the device 2 in assembly. The housing 4 comprises the top covering 6 disposed on the transitional body 8, which is further provided on the refill retainer 10 received over the base section 12. The base section 12 extends to the bottom support 14. The on/off switch 16 protrudes through the switch opening 18 of the top covering 6 for access by a user to control the device 2. In another aspect, it is contemplated that an LED light (not shown) is provided adjacent the on/off switch 16 on the switchboard 30 and protrudes through the top covering 6 in a similar manner. The LED light may indicate the on/off status of the device.

The switchboard 30 is disposed above the motor 32, which is further connected to a central region of the impeller 34 at a rotatable shaft 72 of the motor 32. The impeller 34 is placed in the diverging cone 66 of the transitional body 8. As shown in FIG. 3, the upper end of the diverging cone 66 is provided with the outlet grill 24 defined by the plurality of outlet slots 26 that assist air mixed with chemical treatment to exit the housing 4. The converging cone 64 is connected to the diverging cone 66 at the throat 68, where the joint of the cones 64, 66 define the angle A taken from an exterior surface of the housing 4. The lower end of the converging cone 64 engages the refill retainer 10, specifically against the semicircular wall 50 that provides the ledge 52 for abutting the edge of the converging cone 64. As shown, the chemical substrate 28 comprising the top frame 54, the bottom frame 56 and the fabric substrate 58 secured therebetween, is inserted in the refill retainer 10. The tab 62 protrudes from the housing 4 for easy insertion and removal of the chemical substrate 28.

Still referring to FIG. 3, the base section 12 provides the inlet grill 20 defined by the plurality of inlet slots 22 that permit air to flow into the internal cavity 36 surrounding the battery module 38. The set of battery leads 40 are disposed on an upper end within the battery module 38 and make operative contact with the set of batteries 42 also disposed therein. The battery module 38 is accessible through the module door 44 that is disposed along the surface of the bottom support 14 of the base section 12. It is contemplated that the base section 12, the bottom support 14, and the battery module 38 are manufactured integrally. A plurality of support stands 74 are further provided on the bottom support 14 to engage a resting surface. It is contemplated that four support stands 74 are spaced equally about a perimeter of the bottom support 14 and manufactured integrally with the bottom support 14. In another aspect, the support stands 14 incorporate rubber or other frictional material for resisting lateral movement of the device 2.

Turning now to FIGS. 4 and 5, a front view and a side view of the device 2, respectively, are shown. As shown, the top covering 6, refill retainer 10, base section 12, and the bottom support 14 form a generally cylindrical-shaped profile of the housing 4. The housing 4 angles inward at the transitional body 8 toward the smallest diameter of the housing 4 defined at the throat 68. The chemical substrate 28 disposed within the refill retainer 10 is approximately the same diameter as the retainer 10 and further provides a projecting tab 62 for easy handling of the substrate 28.

Figure 6:
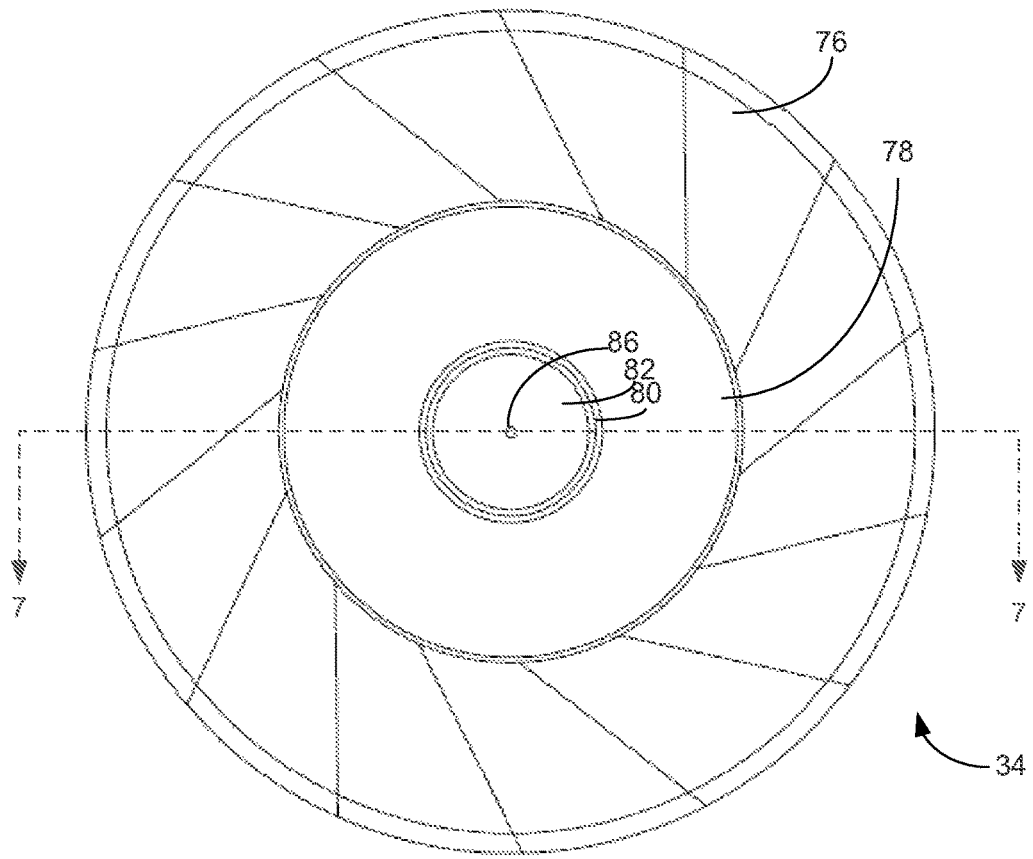
FIG. 6 is a top plan view of an impeller of the dispensing device of FIG. 1.
Figure 7:
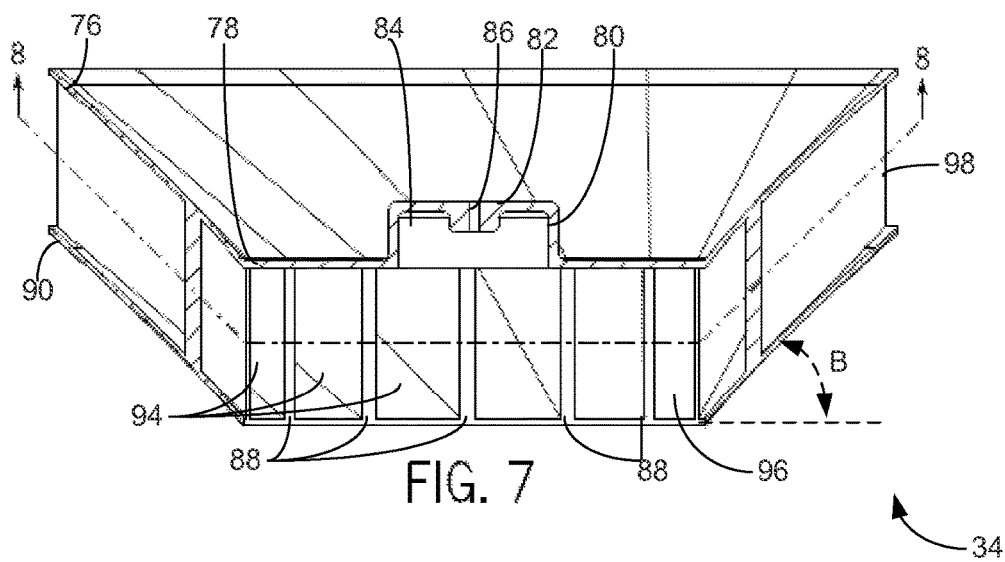
FIG. 7 is a cross-sectional view taken along line 7-7 of FIG. 6.
Figure 8:
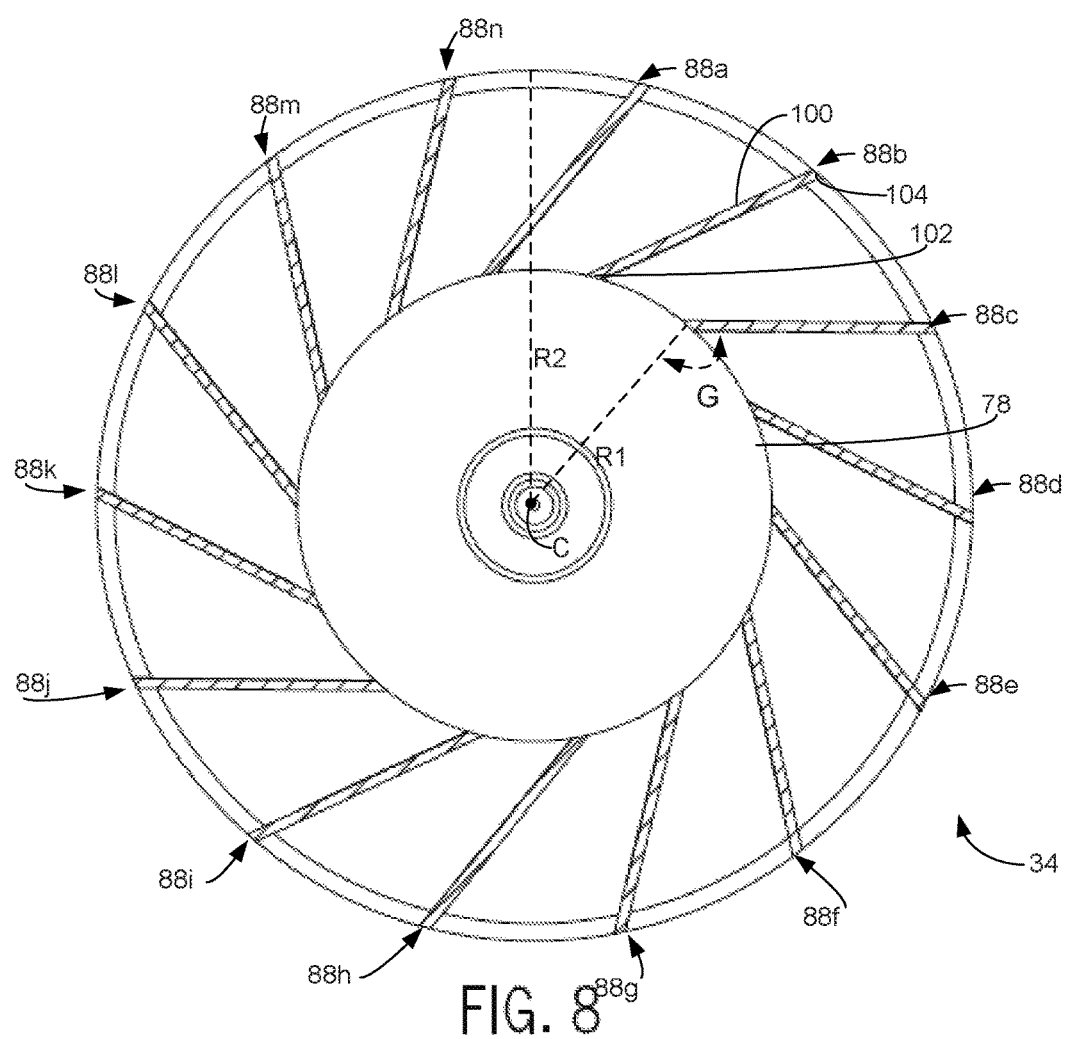
FIG. 8 is a cross-sectional view taken along line 8-8 of FIG. 7.

Moving to FIGS. 6-8, an exemplary embodiment of the impeller 34 is shown. FIG. 6 shows a top view of the impeller 34 that faces the top covering 6 and FIG. 7 shows a cross-sectional view taken along line 7-7 of FIG. 6. A sloped top wall 76 angles downward from a periphery of the impeller 34 and extends to a flat, top central plate 78. Provided on the top central plate 78 is a cylindrical-shaped central vertical wall 80 that extends upward in the direction of the top covering 6 from about a center point of the central plate 78. The central vertical wall 80 joins a top horizontal wall 82 and defines a recess 84 on an underside of the flat central plate 78. It is contemplated that the recess reduces the weight of the impeller 34 and thus reduces start-up and operating electrical loads on the motor 32. The rotatable shaft 72 of the motor 32 is inserted in a tubular opening 86 provided on the top horizontal wall 82 from the top side of the impeller 34 to rotate the impeller 34 during operation.

Further shown in FIGS. 6 and 7, the preferred impeller 34 includes a plurality of fan blades 88 extending between the sloped top wall 76 and a complementary sloped bottom wall 90. It is contemplated that the fan blades 88 do not extend beyond the top wall 76 or the bottom wall 90, although outlines of the fan blades 88 are imparted on the walls 76, 90 when viewed from above as in FIG. 6 or from below. The sloped bottom wall 90 angles downward from the periphery of the impeller 34 following the fan blades 88. As such, a plurality of channels 94 are defined between the plurality of fan blades 88, whereby the moving mixture of air and chemical treatment enters each channel 94 at a channel inlet 96 and exits at a channel exit 98. The plurality of channel exists 98 are aligned with the outlet grill 24 on the transitional body 8 which allows the mixture to escape to a surrounding environment. It is contemplated that the plurality of channels 96, and thus the plurality of fan blades 88, are sloped at an angle B above a plane defined by a lower, inner edge of the sloped bottom wall 90. Preferably, the angle B corresponds to the angle formed by the diverging cone 66 (shown in FIG. 3), which is configured to surround the impeller 34. More preferably, the angle B is approximately 45 degrees. The angle B assists in delivery of the air mixture at an inclined emission angle upon exit from each channel outlet 98, such that the mixture is delivered at approximately 20 degrees to approximately 70 degrees above a plane defined by the top covering 6 of the device 2.

Turning now to FIG. 8, a cross-section taken along lines 8-8 of FIG. 7 shows the impeller 34 comprising fourteen sloped fan blades 88a to 88n (and thus defining fourteen channels 94) although more or less fan blades may be provided. It is contemplated that a configuration having twelve to eighteen flat fan blades results in an ideal balance of airflow and minimal power consumption. Further, it is contemplated that the impeller 34 will operate at about 2000 rpm to about 5000 rpm. The preferred impeller 34 may further include one or more aspects of the fan described in U.S. Patent Application Publication No. 2011/0038761.

FIG. 8 further shows that each blade 88a to 88n has a generally rectangular body 100 extending between an inner edge 102 and an outer edge 104. A radial reference line R1 can be extended from a centerpoint C of the impeller 34 to the inner edge 102 of each blade 88a to 88n, which is provided on the perimeter of the top central plate 78. Likewise, a radial reference line R2 can be extended from the centerpoint C to the outer edge 104 of each blade 88a to 88n. The rectangular body 100 of each blade 88a to 88n forms an included angle G with its associated radial reference line R1. The fan blades 88a to 88n can be angled at the angle G in the direction of rotation of the impeller 34, which rotates about a vertical axis through the centerpoint C. In other embodiments, the fan blades 88a to 88n are angled in a direction opposite to the direction of rotation of the impeller 34. It is contemplated that each blade 88a to 88n has a length extending from the inner edge 102 to the outer edge 104 that measures about 80% to about 120% of the distance of the radial reference line R1, and more preferably about 100% of the distance of the radial reference line R1. Preferably, each blade 88a to 88n has a length extending from the inner edge 102 to the outer edge 104 that measures about 60% to about 90% of the distance of the radial reference line R2, and more preferably about 75% of the distance of the radial reference line R2. In the embodiment shown, it is contemplated that the included angle G which is formed between the rectangular body 100 of each blade 88a to 88n is in the range of 100 degrees to about 150 degrees. More preferably, the included angle G is in the range of about 120 degrees to about 130 degrees. Such example fan sizes and fan blade angles are intended to contribute to an ideal balance of airflow and minimal power consumption for the device 2, although other fan designs can be contemplated as well.

Figure 9:
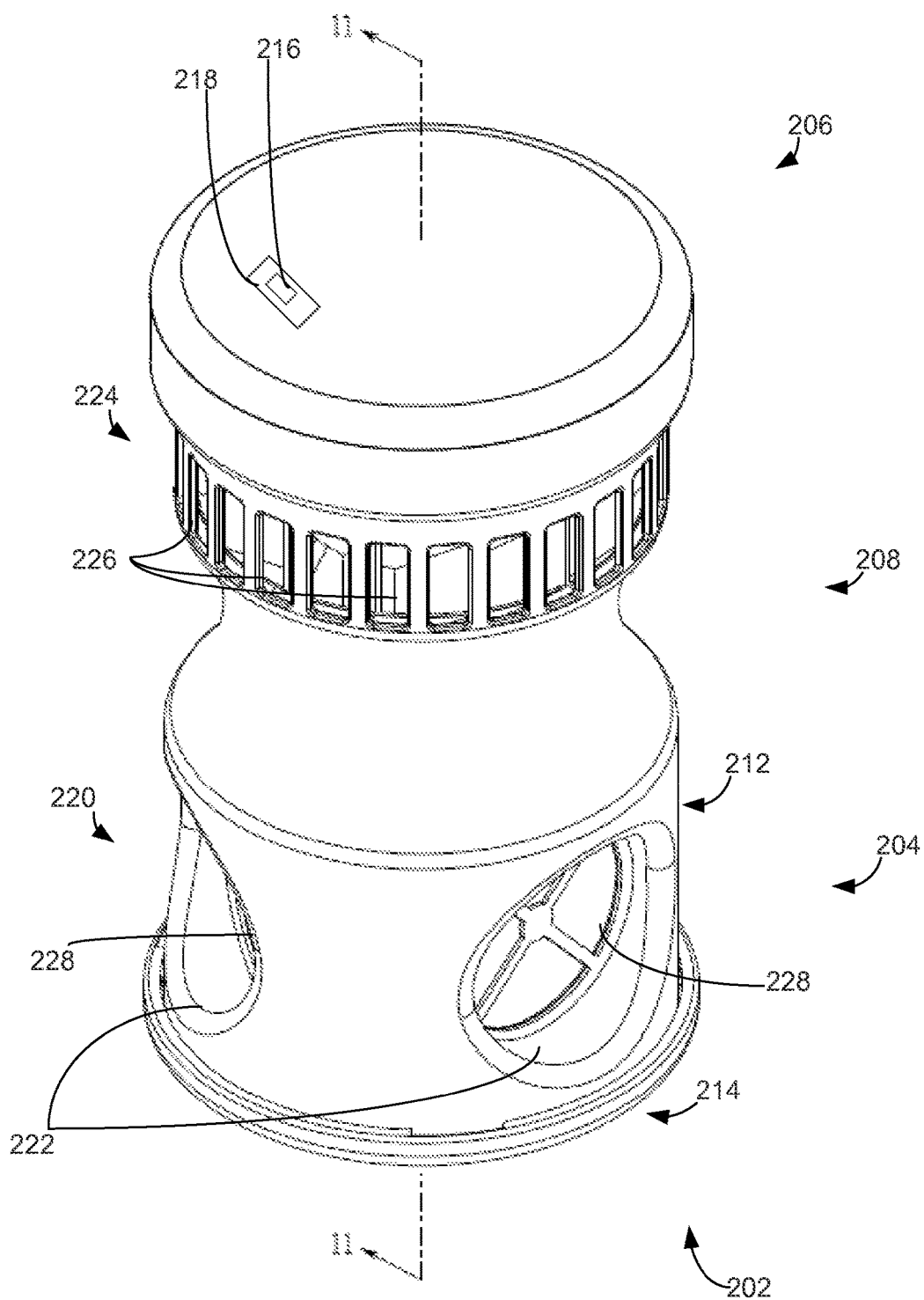
FIG. 9 is a top and side perspective view of a second embodiment of a device for dispensing an air treatment chemical having three chemical substrates.

Moving now to FIGS. 9-14, an alternative embodiment of the device 202 is shown. As shown in FIG. 9, the device 202 includes a housing 204 that comprises a top covering 206 disposed on a transitional body 208. The transitional body 208 is manufactured integrally with a base section 212, which together define an internal space for a refill retainer 210 (shown in FIG. 10). The base section 212 is a cylindrical-shaped structure that extends downward to a bottom support 214. The bottom support 214 is generally a circular-shaped surface transverse to the cylindrical structure and configured to engage a resting surface for setting the device 202, such as a table-top. It is contemplated that the device 202 is easily portable and lightweight. Further, the device 202 can be operated by an on/off switch 216 provided through a switch opening 218 disposed on a portion of the top covering 206 or elsewhere on the housing 204. The configuration of the device 202 in FIG. 9 is illustrative of an exemplary configuration and is not intended to limit the present invention.

Further shown in FIG. 9, an air inlet grill 220 is provided on the cylindrical structure of the base section 212. The inlet grill 220 is characterized by a plurality of spaced-apart circular inlet slots 222 disposed 360 degrees circumferentially around the base section 212. The inlet slots 222 permit outside air to enter the housing 204 and travel upward through the housing 204 to an outlet grill 224 provided on an upper end of the transitional body 208. The outlet grill 224 is generally a cylindrical ring that comprises a plurality of spaced-apart longitudinal outlet slots 226 or ribs disposed 360 degrees circumferentially about the upper end of the transitional body 208. Air flowing within the housing 204 exits the housing 204 through the outlet slots 226. It is contemplated that the inlet slots 222 are circular openings sized corresponding to a plurality of chemical substrates 228 disposed therein and the outlet slots 226 are long, narrow openings. The outlet slots 226 may be smaller than the inlet slots 222, but more numerous and compacted than the inlet slots 222. The present invention, however, is not limited to any particular shapes, sizes, numbers or patterns of openings. For instance, the inlet slots 222 and the outlet slots 226 may extend about any partial or whole portion of the circumference of the housing 204.

Still in reference to FIG. 9, the plurality of chemical substrates 228 secured in the refill retainer 210 within the housing 204 extend about a bottom portion of the housing 204 along the base section 212. Specifically, each chemical substrate 228 is positioned against each inlet slot 222 such that air is vacuumed through each substrate 228 upon entrance into the housing 204. In the particular embodiment shown, three chemical substrates 228 are provided, with each chemical substrate 228 bearing at least one air treatment chemical that mixes into the moving air to be carried through the housing 204 and released outside of the housing 204 when the device 202 is turned on. As such, each of the plurality of chemical substrates 228 is replaceable upon use-up of the air treatment chemical impregnated therein.

Figure 10:
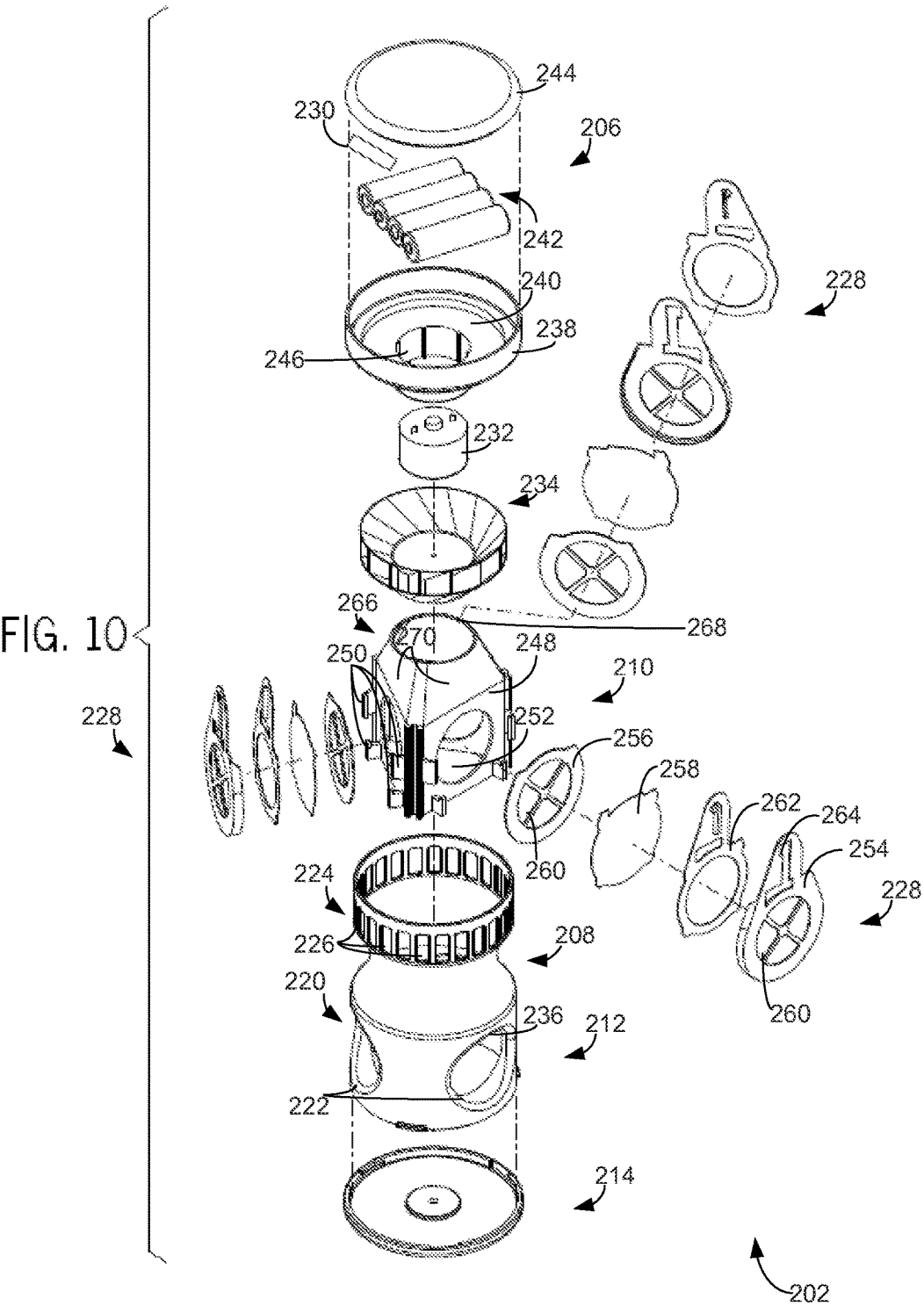
FIG. 10 is an exploded perspective view of the dispensing device of FIG. 9.

Turning now to FIG. 10, an exploded view of the device 202 shown in FIG. 9 is depicted. The top covering 206 is received on an upper portion of the transitional body 208 proximate the outlet grill 224 defined by the plurality of outlet slots 226. The top covering 206 acts as a lid for enclosing a switch board 230, a motor 232, an impeller 234, and a set of batteries 242 mounted between the top covering 206 and the transitional body 208. More particularly, the top covering 206 comprises a battery module 238 having an internally disposed battery platform 240 for placing the set of batteries 242 therein. A module door 244 attaches to the top of the battery module 238 and provides access to the module 38 for replacing batteries and, in some embodiments, for securing the switch board 230 having the on/off switch 16 thereon. Furthermore, a cylindrical motor sleeve 246 is provided extending below the battery platform 240 to secure the motor 232 therein. Various attachment means can be contemplated for securing the module door 244 on the battery module 238, including twist-lock securing, hinges, snaps, and the like. It is noted that although batteries are provided for the present invention, other power supply means can be incorporated, such as solar power.

Still referring to FIG. 10, the transitional body 208 further extends to the base section 212 to enclose the refill retainer 210 disposed therein. As shown, the transitional body 208 and base section 212 are manufactured integrally, although it can be contemplated that they are separable pieces, which may facilitate in changing the chemical substrates 228 as needed. The base section 212 provides the inlet grill 220 defined by the plurality of inlet slots 222 and further extends downward to the bottom support 214 disposed generally transverse thereof. It is contemplated that the bottom support 214 is twist-lock secured to the base section 212, thereby providing easy access to the refill retainer 210 to facilitate the replacement of chemical substrates 228. The base section 212 further defines an internal cavity 236 that receives incoming air through the chemical substrates 228 and into the centrally disposed refill retainer 210.

The refill retainer 210 of FIG. 10 provides a plurality of substrate surfaces 248 for securing the plurality of chemical substrates 228. Each substrate surface 248 comprises a flat wall with a circular cut-out corresponding to the portion of the chemical substrate 228 where airflow is penetrated through. A plurality of protruding substrate guides 250 are disposed on each substrate surface 248 for securing the periphery of the chemical substrate 228 inserted thereon. In the particular embodiment, three chemical substrates 228 are provided on three substrate surfaces 248, which are joined together at the edges to define a triangular platform 252 comprising a solid material extending across the bottom edges of the substrate surfaces 248.

Still in reference to FIG. 10, each of the chemical substrates 228 has a generally slab-like support structure 254 that is essentially tear-drop shaped with a circular portion at one end and a triangular portion at another end for ease in handling the substrate 228. In a particular aspect, the chemical substrate 228 may comprise one of the refill substrates described in U.S. Patent Application Publication No. 2011/0038761. The support structure 254 and a complementary bottom frame 256 each have a circular opening with a spoke support 260 spanning across it, which may aid in positioning a fabric substrate 258 that bears the air treatment chemical. A refill indicator 262 is provided between the fabric substrate 258 and the support structure 254, such that a portion of the indicator 262 is exposed through an indicator slot 264. The refill indicator 262 provides visual notification queues to the user when the chemical substrate 228 needs to be replaced, such as color changes.

When air is drawn in through the inlet slot 222 corresponding to the chemical substrate 228, the air passes through the fabric substrate 258 portion of the chemical substrate 228 and a volume of the air treatment chemical mixes with the moving air. The mixed air continues to flow upward through a converging section 266 of the refill retainer 210 toward a throat 268 defined by an upper edge of the refill retainer 210. In particular, the converging section 266 comprises a plurality of panels 270 extending from the upper end of the substrate surfaces 248 and sloping inward and upward to the throat 268.

Figure 11:
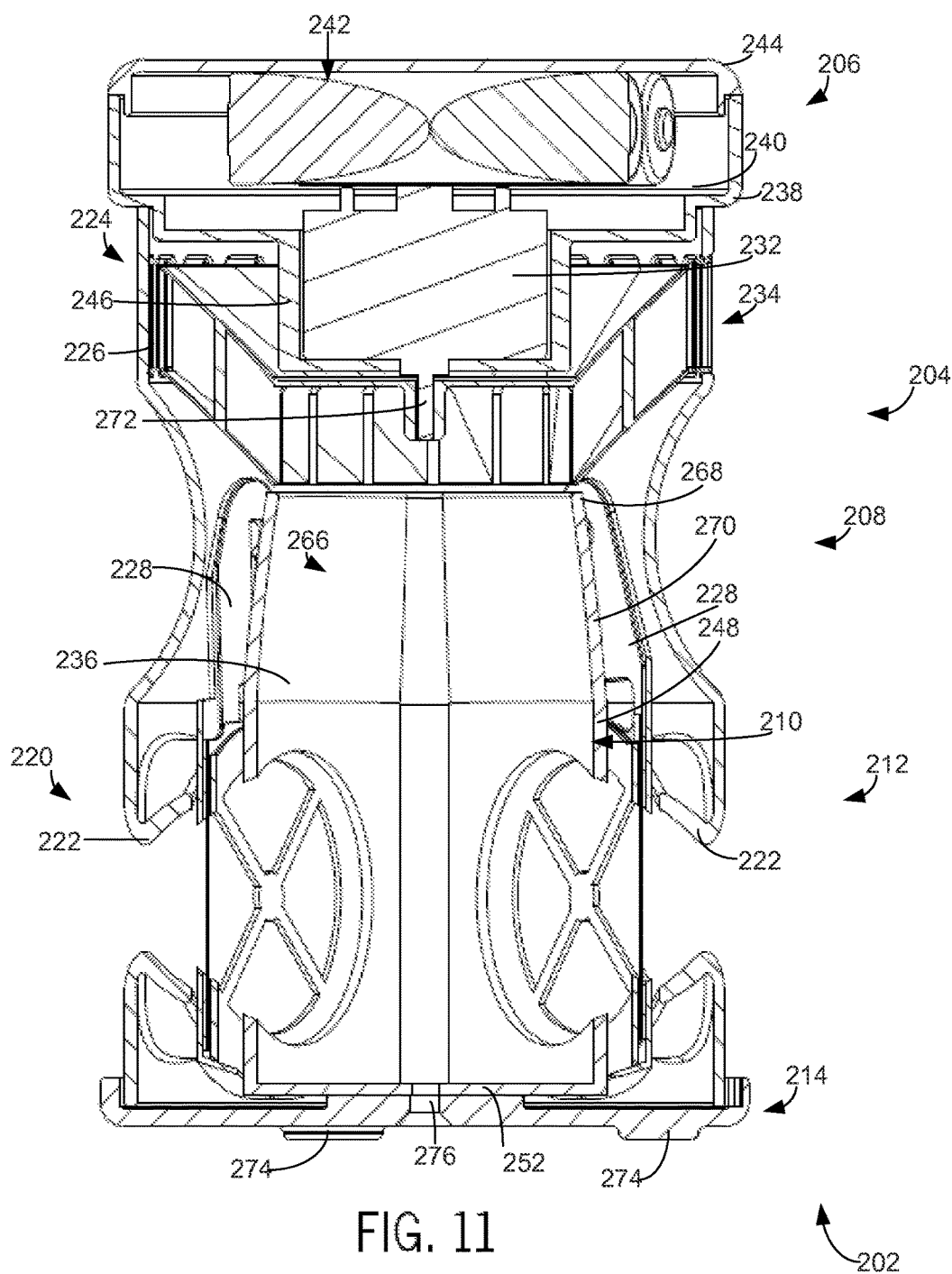
FIG. 11 is a cross-sectional view taken along line 11-11 of FIG. 9.

Turning now to FIG. 11, a cross-section of the device 202 of FIG. 9 taken along lines 11-11 is shown. The assembled housing 204 comprises the two-piece top covering 206 provided over the transitional body 208 that extends to the base section 212, which is secured at a bottom end by the bottom support 214. As shown, the set of batteries 242 is provided between the module door 244 and the battery module 238 of the top covering 6, and particularly on the battery platform 240 extending therein. Extending below the battery platform 240 is the motor sleeve 246 with the motor 232 mounted therein. It is contemplated that the motor sleeve 246 and the battery platform 240 define a continuous space such that a wire can connect the components for transmission of power and electrical signals. A rotatable shaft 272 extends from out of the motor sleeve 246 and engages the impeller 234. It is contemplated that the impeller 234 is similar to the impeller 34 described in FIGS. 6-8. As such, the impeller 234 draws air through the inlet slots 222 of the inlet grill 220 where the incoming air is immediately mixed with the air treatment chemical provided on the three chemical substrates 228 that are retained against the three substrate surfaces 248. The mixed air travel upward through the converging section 266 of the refill retainer 210, the converging section 266 defined by the three inwardly sloped panels 270 that form a top edge defining the throat 268. It is noted that the gradual sloping allows the mixed air to be guided into the impeller 234 and subsequently released from the outlet slots 226 of the outlet grill 224.

Further shown in FIG. 11, a plurality of support stands 274 are further provided on the bottom support 214 to engage a resting surface. It is contemplated that three support stands 274 are spaced equally about a perimeter of the bottom support 214 and manufactured integrally with the bottom support 214. In another aspect, the support stands 274 incorporate rubber or other frictional material for resisting lateral movement of the device 202. The bottom support 214 further comprises a screw orifice 276 configured to receive a screw 278 (see FIG. 14) therein, such that the bottom support 214 cannot be removed from the base section 212 without a tool. This may be beneficial to deter unwanted access to the chemical substrates 228 in the housing 204.

Figure 12:
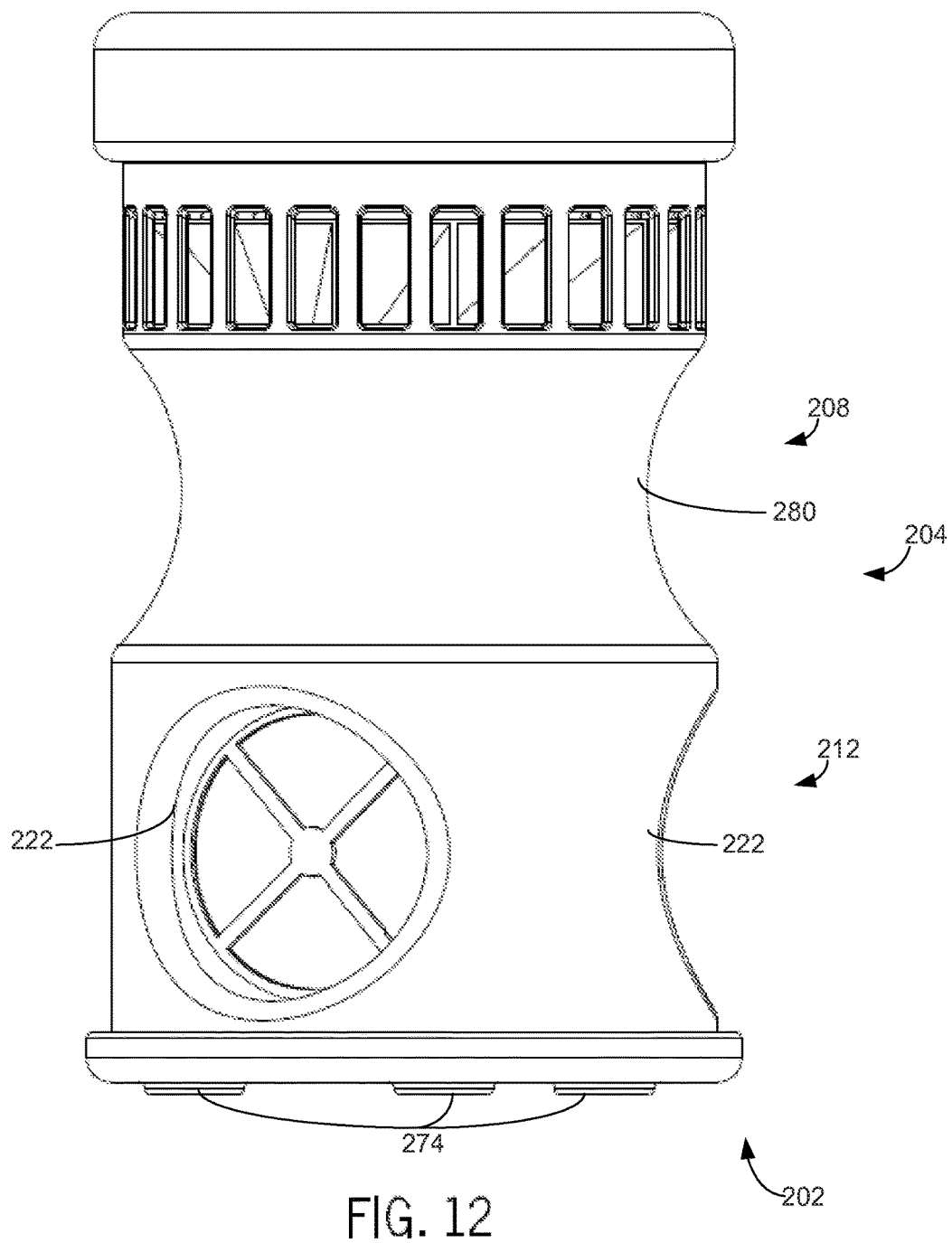
FIG. 12 is a front side view of the dispensing device of FIG. 9.

Referring now to FIGS. 12-14, side views of the device 202 are shown in FIGS. 12 and 13 and a bottom view is shown in FIG. 14. The side views of FIGS. 12 and 13 show that the exemplary embodiment of device 202 generally comprises a cylindrical-shaped profile and is elevated slightly above a flat support surface by the three support stands 274. The inlet slots 222 are concave inward on the base section 212, whereas curved cylindrical walls are spaced between the slots 222. The transitional body 208 is concave inward about 360 degrees of the periphery and defines a neck 280 at its narrowest section. It is contemplated that the neck 280 is adjacent to the throat 268 of the refill retainer 210 disposed within the housing 204. FIG. 14 shows the bottom support 214 having the three equally spaced support stands 274 disposed about a peripheral portion of the support 214. The screw 278 is further secured in the screw orifice 276.

Figure 16:
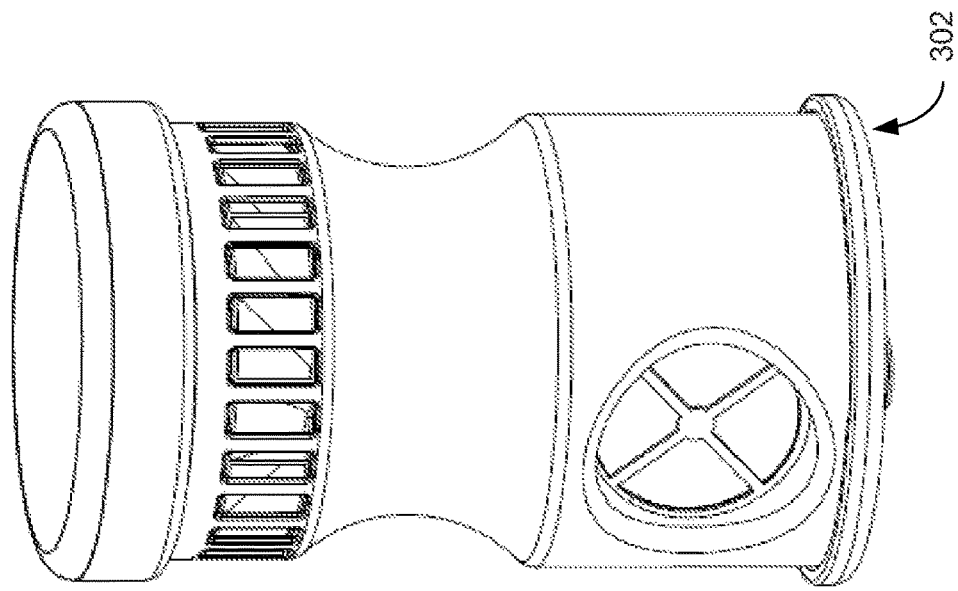
FIG. 16 is a top and left side perspective view of the dispensing device of FIG. 15.
Figure 15:
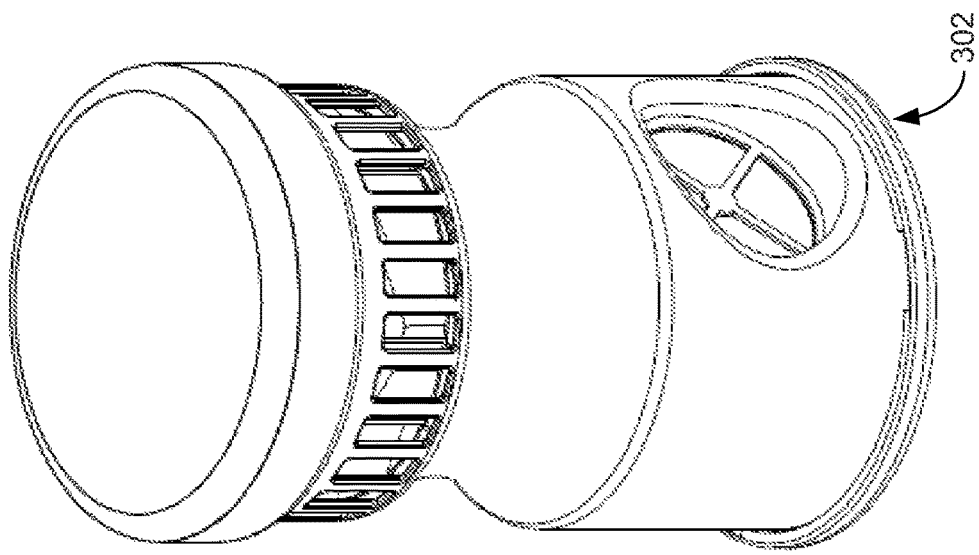
FIG. 15 is a top and right side perspective view of a third embodiment of a device for dispensing an air treatment chemical having two chemical substrates.

FIGS. 15 and 16 show another embodiment of the device 302. The device 302 retains two chemical substrates therein and can be formed similar to the device 202, which retains three chemical substrates. As such, the device 302 may be smaller and lighter than the device 202. It is contemplated that a variety of alternative designs can be implemented with the invention provided herein according to the user's needs.

INDUSTRIAL APPLICABILITY

The dispensing device disclosed herein can be configured to operate in one or more embodiments and combinations thereof to provide an improved user experience having various options for dispensing volatile materials according to various user needs.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications that come within the scope of the appended claims are reserved.

All documents cited in the Detailed Description of the Invention are, in relevant part, incorporated herein by reference; the citation of any document is not to be construed as an admission that it is prior art with respect to the present invention.

We claim:

1. A device for dispensing an air treatment chemical, the device comprising:
    a housing including an exterior wall defining a transitional body, the housing also including an inlet for permitting air to enter into an interior space of the housing, the air inlet comprising a plurality of inlet slots disposed 360 degrees circumferentially about the housing, and the housing including an outlet for permitting air mixed with air treatment chemical to exit the interior space, the air outlet comprising a plurality of outlet slots evenly disposed 360 degrees circumferentially about the housing;
    a substrate positioned within the housing just above the inlet, the substrate bearing the air treatment chemical;
    a power supply mounted within the housing;
    a motor mounted within the housing, the motor being powered by the power supply; and
    an impeller mounted within the housing and connected to the motor, the impeller being capable of moving air from the inlet adjacent the substrate so as to mix the air treatment chemical into the moving air, and then deliver a mixture of air and air treatment chemical through the outlet to outside of the housing,
    wherein the transitional body defines a convergent-divergent channel in which the air mixed with air treatment chemical compresses, at a converging cone section, toward a throat of the convergent-divergent channel and expands, at a diverging cone section, away from the throat and through the outlet of the housing, and
    wherein a lower edge of the converging cone section is positioned entirely above the entire substrate.

2. The device of claim 1, wherein the converging cone section is positioned below the diverging section of the convergent-divergent channel.

3. The device of claim 1, wherein a plurality of substrates are stacked upstream from the lower end of the converging cone section.

4. The device of claim 1, wherein an upper end of the diverging cone section is configured to receive a top cover, the upper end of the diverging cone section further providing a plurality of outlet slots for the outlet.

5. The device of claim 1, wherein the impeller extends through at least a portion of the diverging cone section of the convergent-divergent channel.

6. The device of claim 1, wherein the housing further comprises a refill retainer engaged with the lower edge of the converging cone section and a battery module, the refill retainer configured to receive the at least one substrate or a plurality of substrates in a stacked position.

7. The device of claim 1, wherein the convergent-divergent channel defines a 75 degree to a 105 degree angle between the converging cone section and the diverging cone section, the angle having a vertex at the throat of the channel.

8. A device for dispensing an air treatment chemical, the device comprising:
    a housing including an exterior sidewall defining a convergent-divergent channel, the housing including an inlet for permitting air to enter into an interior space of the housing, the inlet comprising a plurality of inlet slots disposed 360 degrees circumferentially about the housing, and the housing including an outlet for permitting air mixed with air treatment chemical to exit the interior space, the outlet comprises a plurality of outlet slots evenly disposed 360 degrees circumferentially about the housing, and wherein the inlet is provided below the outlet on the housing;
    a substrate positioned within the housing, the substrate bearing the air treatment chemical;
    a power supply mounted within the housing;
    a motor mounted within the housing, the motor being powered by the power supply; and
    an impeller mounted within the housing and connected to the motor, the impeller comprising an enclosed impeller having multiple channels,
    wherein the convergent-divergent channel includes a converging section that contracts in diameter along a length of the sidewall from a lower edge of the converging section to a throat of the convergent-divergent channel and a diverging section that expands in diameter along another length of the sidewall from the throat to the outlet of the housing, and
    wherein the lower edge of the converging section is positioned entirely above the entire substrate.

9. The device of claim 8, wherein the impeller is mounted to a top cover of the housing, the top cover of the housing configured to be received on an upper end of the diverging section of the convergent-divergent channel.

10. The device of claim 8, wherein the multiple channels of the impeller extend through at least a portion of the diverging section of the convergent-divergent channel.

11. The device of claim 8, wherein the multiple channels are sloped parallel to a portion of the sidewall defining the diverging section of the convergent-divergent channel.

12. The device of claim 8, wherein the multiple channels are angled opposite to the direction of rotation of the impeller.

13. The device of claim 8, wherein the multiple channels of the impeller include 10 channels to 20 channels.

14. The device of claim 8, wherein the sidewall defining the convergent-divergent channel defines a 75 degree to a 105 degree angle between the converging section and the diverging section, the angle having a vertex at the throat of the channel.

15. The device of claim 8, the power supply is mounted to a top cover of the housing.

16. The device of claim 8, wherein the power supply is mounted below the substrate positioned within the housing.

17. The device of claim 8, wherein a base portion of the housing includes plurality of inlet slots and receives a plurality of substrates configured to be aligned with the plurality of inlet slots.

18. The device of claim 17, wherein the plurality of substrates comprises two or three substrates.

19. The device of claim 8, wherein the sidewall further defines the plurality of inlet slots and the plurality of outlet slots, wherein both the plurality of inlet slots and outlet slots are orthogonal to a horizontal plane defining a top cover of the housing.

20. A device for dispensing an air treatment chemical, the device comprising:

a housing including an inlet for permitting air to enter into an interior space of the housing and including an outlet for permitting air mixed with air treatment chemical to exit the interior space, the inlet comprising a plurality of inlet slots disposed 360 degrees circumferentially about the housing, and the outlet comprising a plurality of outlet slots evenly disposed 360 degrees circumferentially about the housing;

a plurality of substrates mounted within the housing, each of the plurality of substrates bearing the air treatment chemical, and each of the plurality of substrates being disposed adjacent a separate spaced apart inlet slot of the plurality of inlet slots such that each of the plurality of substrates are in spaced apart relationship;

a power supply mounted within the housing;

a motor mounted within the housing, the motor being powered by the power supply; and an impeller mounted within the housing and connected to the motor, the impeller being capable of moving air from the inlet adjacent the plurality of substrates so as to mix the air treatment chemical into the moving air, and then deliver a mixture of air and air treatment chemical through the outlet to outside of the housing, wherein a refill retainer is disposed within the housing, and the refill retainer defines at least a portion of a convergent-divergent channel defining a flow pathway for the air mixed with air treatment chemical, which compresses at a converging section toward a throat of the convergent-divergent channel and expands at a diverging section away from the throat and through the outlet of the housing, wherein the refill retainer positions each substrate of the plurality of substrates between one inlet slot of the plurality of inlet slots and one cut-out of a plurality of cut-outs defined by the refill retainer;

wherein the impeller delivers the mixture at an inclined emission angle with respect to a plane defined by a top covering of the housing, and wherein the impeller includes multiple channels defined between a plurality of flat fan blades sloped upwardly at an angle with respect to a horizontal plane, each channel having a channel outlet at the outlet of the housing and the channel outlet has an outlet emission angle with respect to a horizontal plane, the angle of the flat fan blades determines the outlet emission angle, and wherein the outlet emission angle ranging from approximately 20 degrees to 70 degrees, and wherein a lower edge of the converging section is positioned entirely above the plurality of substrates.

21. The device of claim 20, wherein the inclined emission angle is 45 degrees.

22. The device of claim 20, wherein the impeller comprises an enclosed impeller, and the multiple channels are sloped parallel to the diverging section of the convergent-divergent channel and angled opposite to the direction of rotation of the impeller.

23. The device of claim 22, wherein the multiple channels of the impeller direct the air with air treatment chemical to exit out of the plurality of outlet slots at an angle directed above the top cover of the housing and away from the plurality of inlet slots.

* * * * *